US008674306B2

(12) United States Patent
Falk et al.

(10) Patent No.: US 8,674,306 B2
(45) Date of Patent: Mar. 18, 2014

(54) GAS SENSING SYSTEM EMPLOYING RAMAN SCATTERING

(75) Inventors: Joel Falk, Pittsburgh, PA (US); Peng Kevin Chen, Wexford, PA (US); Michael Paul Buric, Pittsburgh, PA (US); Steven D. Woodruff, Morgantown, WV (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 75 days.

(21) Appl. No.: 13/300,988

(22) Filed: Nov. 21, 2011

(65) Prior Publication Data

US 2012/0176600 A1    Jul. 12, 2012

Related U.S. Application Data (60) Provisional application No. 61/416,936, filed on Nov. 24, 2010.

(51) Int. Cl.
   *G01N 21/35*    (2006.01)
(52) U.S. Cl.
   USPC .............................. 250/343; 356/51; 356/301
(58) Field of Classification Search
   USPC ....................................................... 250/343
   See application file for complete search history.

(56) References Cited

U.S. PATENT DOCUMENTS

| | | | |
|---|---|---|---|
| 4,222,011 A | 9/1980 | Kurnit | |
| 4,648,714 A | 3/1987 | Benner | |
| 5,450,193 A * | 9/1995 | Carlsen et al. | ................ 356/301 |
| 5,521,703 A | 5/1996 | Mitchell | |
| 7,327,928 B2 | 2/2008 | Shaw et al. | |
| 2006/0038990 A1 * | 2/2006 | Habib et al. | .................. 356/301 |
| 2007/0020144 A1 | 1/2007 | Du et al. | |
| 2008/0268469 A1 | 10/2008 | Srienc et al. | |
| 2009/0059234 A1 | 3/2009 | Dreyer et al. | |
| 2009/0122308 A1 * | 5/2009 | Dong et al. | ................... 356/301 |
| 2009/0257055 A1 * | 10/2009 | Chen et al. | ..................... 356/301 |
| 2010/0007876 A1 | 1/2010 | Chen et al. | |
| 2012/0105827 A1 * | 5/2012 | Carter et al. | .................... 356/51 |

OTHER PUBLICATIONS

J. Kiefer, T Seeger, S Steuer, S Schorsch, M C Weikl, A Leipertz, "Design and characterization of a Raman Scattering—based sensor system for temporally resolved gas analysis and its application in a gas turbine power plant," Meas Sci Technol 19 (2008), 085408.

(Continued)

*Primary Examiner* — Marcus Taningco
(74) *Attorney, Agent, or Firm* — Eckert Seamans Cherin & Mellott, LLC; Philip E. Levy (57) ABSTRACT

A gas detection system includes a light detector, a pump laser with spectral emission between UV and IR wavelengths and structured to generate a laser beam, a hollow waveguide structured to receive a sample gas, the hollow waveguide having a bandwidth sufficient to transmit the laser beam and Stokes Raman photons scattered by the sample gas, and an optical system. The optical system is structured to: (i) direct the laser beam into the hollow waveguide such that it propagates in the hollow waveguide in one or more low-order low-loss waveguide modes, and (ii) direct Raman signals generated within the hollow waveguide in response to the laser beam interacting with the sample gas toward the light detector, the Raman signal including the Stokes Raman photons.

29 Claims, 7 Drawing Sheets

(56) References Cited

OTHER PUBLICATIONS

R. B. Miles, G. Laufer, G.C. Bjorklund, "Coherent anti-stokes Raman scattering in a hollow dielectric waveguide," Appl. Phys. Lett., 30, 417, (1977).

S. M. Howdle, K. Stanley, V.K. Popov, V.N. Bagratashvili, "Can high-pressure Raman spectroscopy be simplified? A microscale optical-fiber capillary cell for the study of supercritical fluids", Applied Spectroscopy, 48, 214, (1994).

S.O. Konorov, A.B. Fedotov, A.M. Zheltikov, R.B. Miles, "Phase-matched four-wave mixing and sensing of water molecules by coherent anti-stokes Raman scattering in large-core-area hollow photonic-crystal fibers", Josa. B., 22, 2049, (2005).

S. D. Schwab, R.L. McCreery, "Remote, long-pathlength cell for high-sensitivity Raman spectroscopy", Applied Spectroscopy, 41, 126, (1987).

T. Ritari, J. Tuominen, H. Ludvigsen, J. C. Petersen, T. Sorensen, T.P. Hansen and H.R. Simonsen, "Gas sensing using air-guiding photonic bandgap fibers", Optics Express, 12, 4080 (2004).

S.O. Konorov, C.J. Addison, H.G. Schulze, R.F.B. Turner, M.W. Blades, "Hollow-core photonic crystal fiber-optic probes for Raman spectroscopy", Optics Letters, 31, 1911 (2006).

Joannopoulos, J., Johnson, S., Winn, J., Meade, R., "Photonic Crystals, molding the flow of light", Chapter 9, Photonic Crystal Fibers, pp. 159-189, Princeton, 2008.

Benabid, F., Hollow-core photonic bandgap fiber—New light guidance for science and technology, Philosophical transactions of the Royal Society, 2006.

10. Komachl, Y., and Sato, H., "Raman probe using a single hollow waveguide", Optics Letters, Nov. 2005, vol. 30, No. 21.

William F. Pearman, J. Chance Carter, S. Michael Angel, and James Wai-Jeung Chan, "Multipass Capillary Cell for Enhanced Raman Measurement of Gases," Appl. Spec. 62, 285 (2008).

F. Benabid, F. Couny, J. C. Knight, T. A. Birks, P. St J. Russell, "Compact, stable and efficient all-fibre gas cells using hollow-core photonic crystal fibres", Nature, vol. 434, pp. 488-491 (2005).

M. Buric, K. Chen, J. Falk, and S. Woodruff. "Improved Sensitivity Gas Detection by Spontaneous Raman Scattering." Applied Optics, 2009.

M. Buric, K. Chen, J. Falk, and S. Woodruff. "Improved Sensitivity Spontaneous Raman Scattering Multi-Gas Sensor." Conference on Lasers and Electro-optics, 2009.

N. Ayyalasomayajula, M. Buric, K. Chen, J. Falk, Hornak, and S. Woodruff. "A Novel Raman-Based Sensor System for Analysis of Gaseous Fuels," Submitted to IEEE Sensors, 2009.

M. Buric, K. Chen, J. Falk, R. Velez, and S. Woodruff. "Raman Sensing of Fuel Gases Using a Reflective Coating Capillary Optical Fiber." SPIE Symposium on Defense, Security + Sensing, Apr. 2009.

M. Buric, J. Falk, K. Chen, and S. Woodruff. "Enhanced Spontaneous Raman Scattering Using a Photonic Crystal Fiber." Conference on Lasers and Electro-optics, 2008.

S. Wooduff, M. Buric, K. Chen, and J. Falk. "Photonic-Fiber Raman Spectroscopy for Real-Time, Gas-Composition Analysis." Laser Applications to Chemical, Security, and Environmental Applications, 2008.

M. Buric, K. Chen, J. Falk, and S. Woodruff. "Photonic-Bandgap-Fiber Sensors for Gas Detection." Trends in Photonics, 2008, Research Signpost.

Buric, Michael P., et al., Metal-lined capillaries for efficient Raman gas sensing, Lasers and Electro-Optics (CLEO) and Quantum Electronics and Laser Science Conference (QELS), 2010 Conference on May 16-21, 2010. Whole document.

* cited by examiner

GAS SENSING SYSTEM EMPLOYING RAMAN SCATTERING

CROSS-REFERENCE TO RELATED APPLICATIONS

This application claims priority under 35 U.S.C. §119(e) from provisional U.S. patent application No. 61/416,936, entitled "Gas Sensing System Employing Raman Scattering" and filed on Nov. 24, 2010, the contents of which are incorporated herein by reference.

GOVERNMENT CONTRACT

This invention was made with government support under grant # DE-AC26-04NT41817 awarded by the DOE. The government has certain rights in the invention.

BACKGROUND OF THE INVENTION

1. Field of the Invention

The present invention relates to gas sensing systems, and in particular, to an optical system for identifying, characterizing and/or determining the concentration of various gases in a gas mixture or sample that employs Raman scattering.

2. Description of the Related Art

The detection and characterization of molecular gases in a given sample is a relatively difficult challenge. Usually, this task is relegated to expensive and time consuming processes like mass spectrometry and gas chromatography. Furthermore, numerous industrial applications require such gas-phase analysis for pollution and process control. For example, in large natural gas-fired turbine electricity generators, large quantities of natural gas are mixed with air and burned. Because natural gas comes from a variety of sources, the composition of the gas changes often. If the composition of natural gas were known a-priori, turbine efficiency could be improved by adjusting the fuel/air mixture and other operating parameters. This control capability requires measurement of the components of the natural gas to better-than 0.1% accuracy, with the measurement being performed at least once every second. There is currently no commercially available sensor or sensing system that is able to measure all of the natural-gas components in one second.

There is thus a need for a sensor and/or sensing system that is able to quickly and reliably identify, characterize and/or determine the concentration of various gases in a gas mixture or sample, such as, without limitation, natural gas burned in a natural gas-fired turbine electricity generator.

SUMMARY OF THE INVENTION

In one embodiment, a gas detection system is provided that includes a light detector, a pump laser with spectral emission between UV and IR wavelengths and structured to generate a laser beam, a hollow waveguide structured to receive a sample gas, the hollow waveguide having a bandwidth sufficient to transmit the laser beam and Stokes Raman photons scattered by the sample gas, and an optical system. The optical system is structured to: (i) direct the laser beam into the hollow waveguide such that it propagates in the hollow waveguide in one or more low-order low-loss waveguide modes, and (ii) direct Raman signals generated within the hollow waveguide in response to the laser beam interacting with the sample gas toward the light detector, the Raman signal including the Stokes Raman photons.

In another embodiment, a gas detection system is provided that includes a light detector, a hollow waveguide structured to receive a sample gas, a laser structured to generate a linearly polarized laser beam, a polarization-converting element structured to receive the linearly polarized laser beam and convert the linearly polarized laser beam into a TE polarized laser beam, and an optical system structured to: (i) direct the TE polarized laser beam into the hollow waveguide, and (ii) direct Raman signals generated within the hollow waveguide in response to the TE polarized laser beam interacting with the sample gas toward the light detector.

In still another embodiment, a gas detection method is provided that includes steps of introducing a sample gas into a hollow waveguide, generating a linearly polarized laser beam, converting the linearly polarized laser beam into a TE polarized laser beam, directing the TE polarized laser beam into the hollow waveguide, receiving Raman signals generated within the hollow waveguide in response to the TE polarized laser beam interacting with the sample gas, and analyzing the Raman signals and identifying one or more particular gases present in the sample gas.

In still a further embodiment, a gas detection system is provided that includes a light detector, a hollow metal-lined capillary waveguide structured to receive a sample gas, the capillary waveguide having an end facet including a metal lining portion and a glass wall portion, capillary waveguide including an additional metal layer provided on the glass wall portion of the end facet, a laser structured to generate a laser beam, and an optical system structured to: (i) direct the laser beam into the capillary waveguide, and (ii) direct Raman signals generated within the capillary waveguide in response to the laser beam interacting with the sample gas toward the light detector.

In yet a further embodiment, a gas detection system is provided that includes a hollow waveguide structured to receive a sample gas, the hollow waveguide having an end facet, a laser structured to generate a laser beam, an optical system structured to direct the laser beam into the hollow waveguide, and a dispersive element. The optical system is also structured to direct Raman signals generated within the hollow waveguide in response to the laser beam interacting with the sample gas toward the dispersive element, and the dispersive element is structured to produce a spectrally-dispersed image of the end-facet of the hollow waveguide, wherein the spectrally-dispersed image of the end-facet of the hollow waveguide will contain both gas-Raman signals and silica-Raman noise. The system also includes a digital image capture device structured to generate a digital version of the spectrally-dispersed image of the end-facet, and a computing device operatively coupled to the digital image capture device, the computing device being structured to apply a spatial filtering algorithm to the digital version of the spectrally-dispersed image of the end-facet to subtract out at least a portion of the silica-Raman noise from the digital version of the spectrally-dispersed image.

In still another embodiment, a gas detection method is provided that includes steps of introducing a sample gas into a hollow waveguide, the hollow waveguide having an end facet, generating a laser beam, directing the laser beam into the hollow waveguide, producing a spectrally-dispersed image of the end-facet of the hollow waveguide, wherein the spectrally-dispersed image of the end-facet of the hollow waveguide will contain both gas-Raman signals resulting from interaction between the sample gas and the laser beam and silica-Raman noise, generating a digital version of the spectrally-dispersed image of the end-facet, spatially filtering the digital version of the spectrally-dispersed image of the end-facet to subtract out at least a portion of the silica-Raman noise from the digital version of the spectrally-dispersed image and produce a spatially filtered signal, and analyzing the spatially filtered signal and identifying one or more particular gases present in the sample gas.

In yet a further embodiment, a gas detection system is provided that includes a light detector, a hollow waveguide structured to receive a sample gas, the hollow waveguide having a core portion and an end facet, a laser structured to generate a laser beam, and an optical system structured to: (i) direct the laser beam into the hollow waveguide, and (ii) direct Raman signals generated within the hollow waveguide in response to the laser beam interacting with the sample gas toward the light detector, wherein the optical system includes a physical aperture located in a plane positioned to receive an image of the waveguide end-facet, wherein the physical aperture is sized such that a first portion of the image containing light from the core portion will be passed through the physical aperture toward the light detector while a second portion of the image containing light emanating from outside the core portion is blocked.

In still a further embodiment, a gas detection system is provided that includes a light detector, a hollow multimode waveguide structured to receive a sample gas, the waveguide having one or more low order-waveguide modes, each of the low order-waveguide modes having a respective low order propagation angle associated therewith, a laser beam generating component structured to generate a collimated laser beam having a predetermined beam diameter, and a lens structured to: (i) receive the laser beam, (ii) focus the laser beam into the hollow waveguide, and (iii) collect Raman signals generated within the hollow waveguide in response to the collimated laser beam interacting with the sample gas and direct the Raman signals toward the light detector, wherein the predetermined beam diameter is such that when the laser beam reaches the lens, the lens will cause the focused laser beam to enter the hollow waveguide at an angle that excites at least one of the one or more low order-waveguide modes.

In another alternative embodiment, a gas detection method is provided that includes introducing a sample gas into a hollow multimode waveguide, the hollow multimode waveguide having one or more low order-waveguide modes, launching a laser beam into the hollow waveguide at an angle such that the laser beam couples into at least one of the one or more low order-waveguide modes, receiving Raman signals generated within the hollow waveguide in response to the laser beam interacting with the sample gas, and analyzing the Raman signals and identifying one or more particular gases present in the sample gas.

In still another alternative embodiment, a gas detection system is provided that includes a hollow waveguide structured to receive a sample gas, a laser structured to generate a laser beam, and an optical system structured to: (i) direct the laser beam into the hollow waveguide, and (ii) collect and transmit along an optical path Raman signals generated within the hollow waveguide in response to the laser beam interacting with the sample gas. The system also includes a plurality dichroic beam splitters spaced along the optical path, wherein each beam splitter is structured to reflect light of a respective particular Raman peak and to pass all other light, and a plurality of detectors, each one of the detectors corresponding to a respective one of the beam splitters and being positioned to receive the light reflected by the respective one of the beam splitters.

Finally, in still a further alternative embodiment, a gas detection system is provided that includes a light detector, a hollow waveguide structured to receive a sample gas, a laser structured to generate a laser beam and an optical system structured to: (i) direct the laser beam into the hollow waveguide, and (ii) collect Raman signals generated within the hollow waveguide in response to the laser beam interacting with the sample gas direct the Raman signals along an optical path. The system also includes a tunable, rotatable filter positioned in the optical path between the optical system and the light detector, the tunable, rotatable filter including a first filter and a second filter provided on a rotatable platform, wherein a longitudinal axis of the first filter is offset from a longitudinal axis of the second filter by an angle $\theta$, and wherein rotation of the platform alters a wavelength that is passed by the tunable, rotatable filter.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

As described in greater detail herein, the present invention provides an optical Raman scattering gas detection system. As is known in the art, Raman scattering is an optical process by which a pump-laser beam is incident upon a sample (gas or liquid in the case of the present invention) and interacts with that sample. In response, the sample scatters Raman photons in all directions at wavelengths that are different than the pump-laser beam wavelength. The wavelengths of the Raman photons are determined by the constituent molecules of the sample. In addition, the strength of each of the scattered signals is proportional to the concentration of each of the constituents of the sample. As described in greater detail herein, the system of the present invention employs a hollow waveguide which contains the sample gas and wherein the sample gas interacts with a laser beam and produces Raman photons indicative of the gaseous components. The hollow waveguide collects a large number of scattered Raman photons, and efficiently transfers those photons to a spectrometer or other detector where they can be measured and used to identify the sample and its constituents. Furthermore, there are two main sources of noise in the system of the present invention: (i) fluorescence noise from various plastic components found near the optical path (such as the jacket of the waveguide which is usually plastic), and (ii) silica Raman noise which is generated both by the lenses in the optical train and the waveguide walls themselves. Several techniques are described herein for mitigating these noise sources to provide a system with a high signal-to-noise-ratio (SNR), short sampling times, high accuracy, and/or multi-gas measurement while maintaining high gas-Raman signal throughput.

Figure 1:
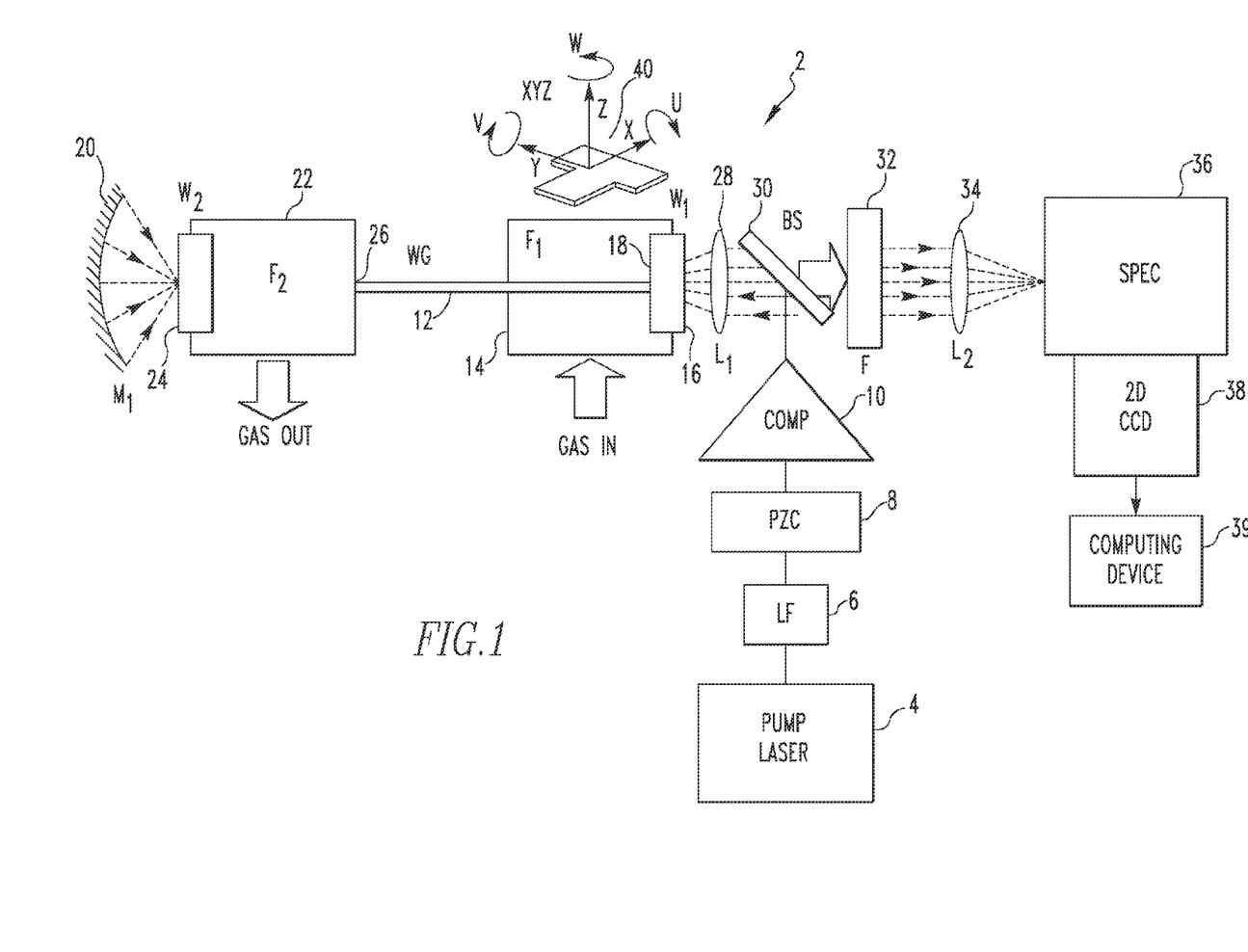
FIG. 1 is a schematic diagram of a gas detection system according to one exemplary embodiment of the present invention.

FIG. 1 is a schematic diagram of a gas detection system 2 according to one exemplary embodiment of the present invention. Gas detection system 2 comprises a special optical train that was designed to optimize light production and collection when using a large multimode metal-lined capillary waveguide. This optical train allows for the collection and measurement of large optical Raman signals, which produces high SNRs, and is comprised of several lenses that are optimized to perform two simultaneous functions. The first function is to launch the excitation laser beam down the capillary so that it couples into the lowest-order capillary waveguide mode or several low-order low-loss waveguide modes and propagates with low-loss. The second function is to collect a large number of propagating Raman modes propagating at a large range of angles (from 0 to several tens-of-degrees) with respect to the capillary length axis (the importance of collecting rays that propagate at large angles in a waveguide Raman system has heretofore not been recognized).

Referring to FIG. 1, gas detection system 2 includes a pump laser 4. In the exemplary embodiment, pump laser 4 exhibits an output wavelength in the UV to near IR wavelength range depending on the application. A narrow-band pump laser line cleanup filter 6 is coupled to pump laser 4. Cleanup filter 6 removes spontaneous emission, plasma, or other optical noise produced by pump laser 4 at wavelengths longer or shorter than the primary pump laser frequency. A linear to azimuthal polarization converter 8 is coupled to the output of cleanup filter 6. The function of linear to azimuthal polarization converter 8 is described in greater detail elsewhere herein. An optical compressor 10 is coupled to linear to azimuthal polarization converter 8. Optical compressor 10 reduces the size of the pump beam to ensure that it propagates as a low-order (low loss) waveguide mode (or several low-loss waveguide modes), regardless of the selection of focal-length of lens 28.

Gas detection system 2 further includes a hollow metal-lined capillary waveguide 12. A high-pressure gas-input flange 14 having a broadband AR coated fused silica window 16 coupled thereto is provided at an input end 18 of capillary waveguide 12. Also, a spherical mirror 20 is positioned $f_{m1}$ (the focal length of spherical mirror 20) away from the opposite end 26 of the capillary waveguide 12. Spherical mirror 20 directs the residual pump light from pump laser 4 (directed into capillary waveguide 12 in the manner described below) and the Raman light generated within capillary waveguide 12 which propagates in the forward-scattering direction back into capillary waveguide 12 and towards the detector described below (spectrometer 36). Use of spherical mirror 20 allows capillary waveguide 12 to operate in a 2-pass configuration. In the case of a multimode capillary waveguide 12, the waveguide causes coupling of the residual pump beam into modes orthogonal to the forward propagating pump modes, which mitigates feedback-induced instabilities in pump laser 4. A high-pressure gas-output flange 22 having a broadband AR coated fused silica window 24 coupled thereto is provided at an output end 26 of capillary waveguide 12 in order to allow pressurization of the capillary waveguide 12 and regulation of the differential gas pressure (and therefore gas flow) across the length of the capillary.

Gas detection system 2 also further includes a high-numerical aperture (NA), large diameter lens 28, a dichroic long-pass beam splitter 30, a laser rejection filter (long-pass or notch) 32 positioned after dichroic beam splitter 30, a focusing lens 34, a dispersive imaging fixed-grating spectrometer 36 and a 2-dimensional CCD camera 38 coupled to the output of the spectrometer 36 (or another suitable detection system such as a series of dichroic beamsplitters and single channel detectors, an array of wavelength-selective detectors, or any such system designed to spectrally separate and simultaneously measure the collected Raman emissions from different molecular sample components). Lens 28 is positioned in front of capillary waveguide 12 f1 (the focal length of lens 28) away from input end 18 of capillary waveguide 12. The function of each of these components within gas detection system 2 is described below. In particular, lens 28 both collects and collimates the Raman output from capillary waveguide 12 in the backscattering-direction and focuses the pump beam from pump laser 4 into capillary waveguide 12. In one exemplary embodiment, the numerical aperture of lens 28 is ~0.25 and the diameter of lens 28 is 25.4 mm. Suitable NA values for lens 28 range between 0.2 and 0.5 and suitable diameters for lens 28 range between 25 and 50 mm. Dichroic long-pass beam splitter 30 reflects the shorter-wavelength pump beam into capillary waveguide 12 (through lens 28) and passes the Stokes-shifted gas-Raman signals with low loss generated within capillary waveguide 12 (and collimated by lens 28) on to lens 34. Laser rejection filter 32 provides a second stage of filtration after the dichroic long-pass beam splitter 30 to remove any remaining pump light from the signal path if present in sufficient quantity due to the backscattering properties of the waveguide and/or imperfect beamsplitter operation. In the exemplary embodiment, focusing lens 34 is positioned f1+f2 away from lens 28 and f2 (the focal length of lens 34) away from the input of spectrometer 36 aperture to facilitate rigorous imaging of the capillary. Focusing lens 34 re-focuses the Raman light and produces an image of the core modes of capillary waveguide 412 at the input of spectrometer 36.

As described above, gas detection system 2 employs a high-pressure windowed flange (in the form of high-pressure gas-input flange 14 having a broadband AR coated fused silica window 16 coupled thereto) to allow high-pressure gases (between slightly above ambient and 800 psia limited by the failure-strength of the capillary 12) to be analyzed to be introduced into hollow metal-lined capillary waveguide 12. In the exemplary embodiment, high-pressure gas-input flange 14 is basically a metal fitting with broadband AR coated fused silica window 16 on one end and a port for a Swagelok or similar capillary ferrule on the other. Another port is provided on the side of the flange to which is connected a flexible tube to supply sample gases. The other end of the capillary waveguide 12 is fitted with a high-pressure gas-output flange 22 which is maintained at a lower absolute pressure than high-pressure gas-input flange 14, such that gases flow continuously through the capillary waveguide 12 while sampling occurs. As seen in FIG. 1, high-pressure gas-input flange 14 is mounted on a 5-axis (or 3-axis) motion stage 40 which allows optimization of the optical coupling by precisely positioning capillary waveguide 12 with respect to the optical train described previously. The combination of motion-stage 40 that positions high-pressure gas-input flange 14 along with capillary waveguide 12 allows for operation of a functional continuously flowing-gas Raman system in one exemplary embodiment of the present invention.

Figure 8:
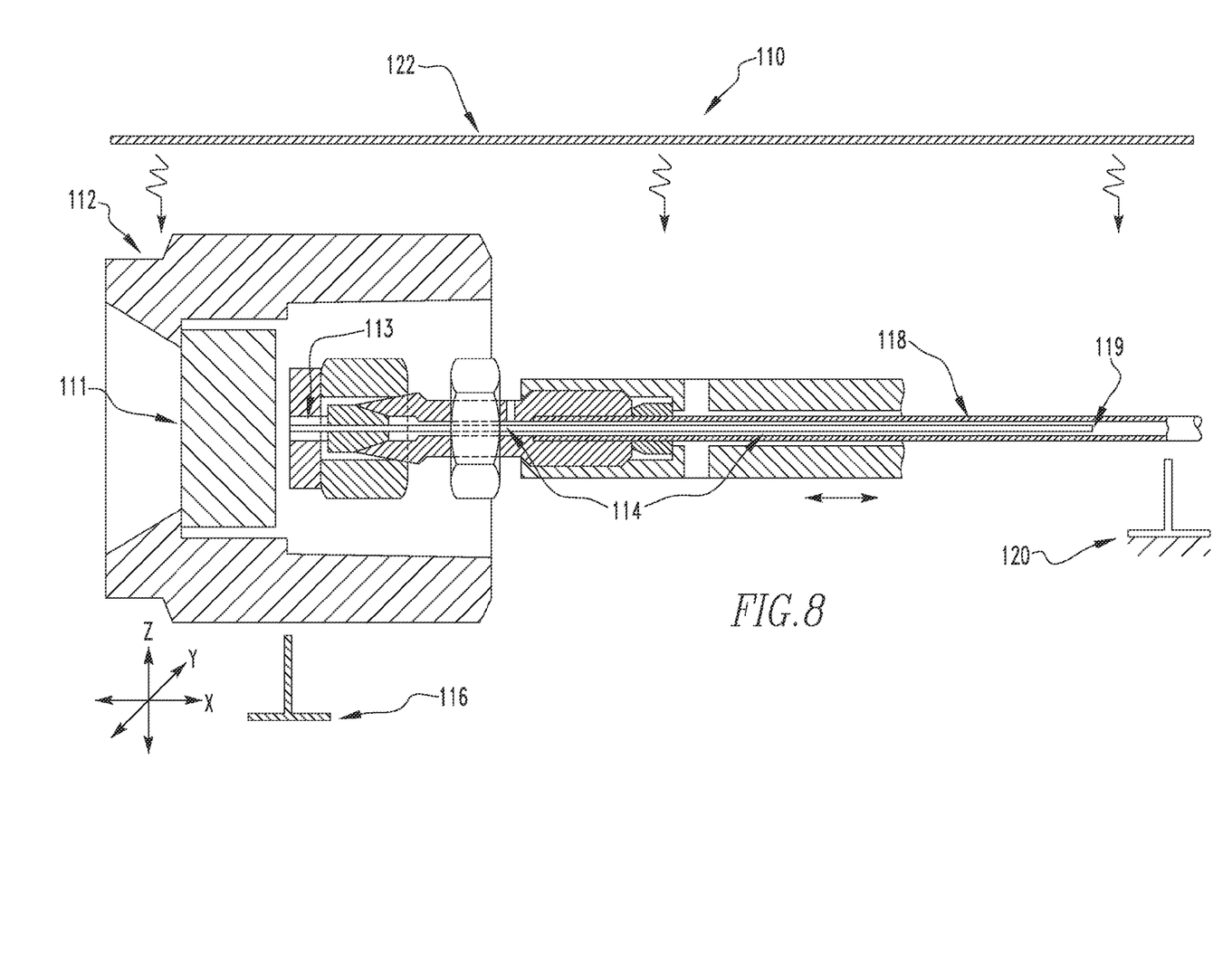
FIG. 8 is a schematic diagram of a temperature-invariant waveguide containment cell that may employed according to an alternative embodiment of the present invention.

In another exemplary embodiment of the present invention, the gas detection system 2 utilizes a temperature-invariant waveguide containment cell 110 shown schematically in FIG. 8. Therein, a single high-pressure windowed flange 112 having a window 111 is utilized to fix one end 113 of a capillary 114 (substituted for waveguide 12 in FIG. 1) with respect to the other optical components of the gas detection system 2. In the exemplary embodiment, flange 112 is mounted on a multi-axis positioning stage 116 to permit accurate alignment of capillary 114 (the waveguide) in the optical system as described in the preceding paragraph. The back side of the high-pressure flange 112 terminates in a length of support tubing 118 constructed of the same material as the high-pressure flange 112. The inner diameter of support tubing 118 is slightly larger than the outer diameter of capillary 114 (the waveguide), thus allowing capillary 114 to slide freely inside support tubing 118 (see sliding capillary end 119), but ensuring that capillary 114 is still held straight to avoid bending losses. The other end of the support tube (spaced from flange 112) is maintained under constant tension by a fixed mount 120 such that it also remains straight. Sample gasses flow through capillary 114 and into support tubing 118, and then exit the other end of the support tubing 118. Heating elements 122, such as heat tracing wire, are applied to the outside of the high-pressure flange 112 and to the length of support tubing 118 to uniformly elevate the temperature of capillary 114 and support structures (support tubing 118). Because the coefficients of expansion are different by roughly a factor of 10 for glass waveguides and metal containment structures, heating the system causes the support structures (support tubing 118) to lengthen at a considerably faster rate than capillary 114. The use of the single-ended waveguide connection and a support-tube which maintains waveguide straightness during expansion and contraction maintains optical alignment stability with changing temperatures and makes the waveguide cell alignment "invariant" to temperature change. The ability to heat the waveguide sample cell permits both stabilization of the waveguide at an elevated temperature for more accurate measurement, as well as creating the possibility of elevating the cell temperature to measure species which are liquids at room temperature.

According to one exemplary embodiment, gas detection system 2 may be configured to optimize the Raman signal collection as follows. Firstly, one determines the minimum necessary resolution for the instrument to be constructed. This minimum optical resolution measures how close in wavelength two independent lines generated by different gas species can be while still being individually measured. Complete spectra can be deconvolved or analyzed with a Principal Component analysis technique to resolve gas-Raman lines that partially overlap. Once the minimum necessary detection resolution is determined (either by trial and error or rigorous statistical quantification) a detector system (e.g., spectrometer 36 and CCD 38) must be specified. The sensitivity of that detector system is chosen such as to provide the necessary detection limit and dispersion required to support the minimum detectable resolution. The dispersion of the detection system must also support observation of the species to be detected over their range of Raman emission wavelengths. The detector will then be characterized by its étendue—i.e.— the product of its entrance aperture size (or slit area in some cases) and entrance aperture angle or f-number.

Figure 1A:
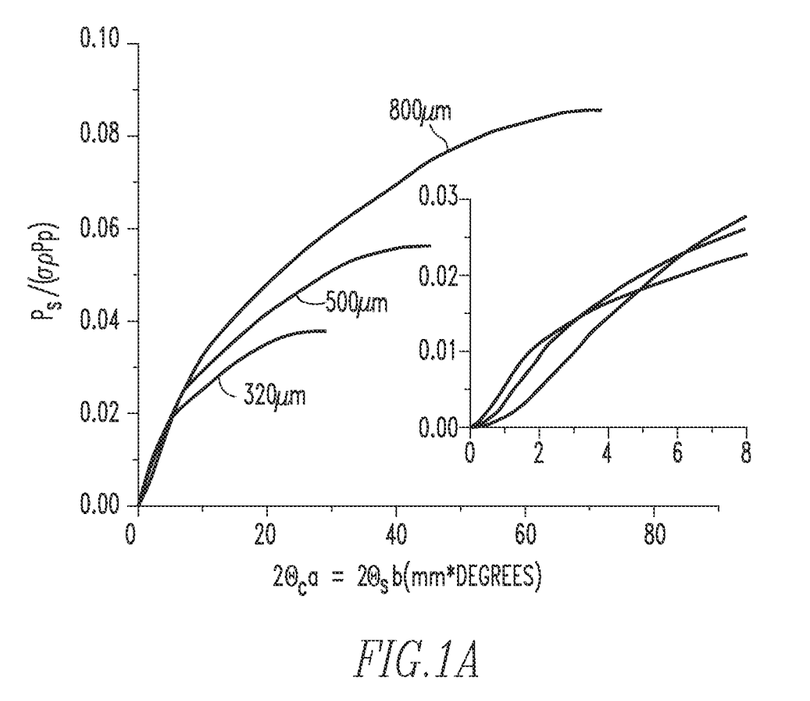
FIG. 1A is a plot of a simulation used to choose an optimal waveguide diameter for a given detector.

Next, an optimally sized capillary waveguide 12 is chosen to provide the highest optical power transferring capabilities to the detection system. FIG. 1A was generated using a mathematical algorithm for calculating the loss in a given reflective hollow waveguide, and integrating that loss to provide a measure of the total emitted Raman power per unit angle. Waveguides of several available inner-diameters are shown on the graph. One then plots the product of the detection aperture-width and the detection entrance angle (½angle in the figure) as a vertical line in the graph. The simulated-power plot that crosses this vertical line at the largest power value (or position on the y-axis of the plot) will indicate the waveguide diameter that will most optimally match the detection aperture. In the case where higher gas transfer rates are required and higher detection limits are not a problem, one may choose a capillary with a larger diameter than the optimal size to foster faster gas flow and smaller collected signals. The length of the chosen waveguide will then be determined by a combination of the necessary detection limits and gas-transfer rate. Lengthening the waveguide is useful in increasing the interaction length and producing larger signals, but returns diminish at some point (because of the backscattering collection) and no additional useful signal is gained beyond a few meters length. The ultimate size of the instrument will be determined by waveguide length, and therefore length will be largely limited by sensor-size.

Once a detection aperture width and capillary waveguide diameter have been determined, the system magnification of gas detection system 2 can be specified. As shown in FIG. 1 and described elsewhere herein, lenses 28 and 34 are used in an imaging configuration to provide an image of the end-facet of capillary waveguide 12 on the entrance aperture of spectrometer 36. The system magnification in this case is $M=f2/f1$ (where f2 is the focal length of lens 34 and f1 is the focal length of lens 28), and the size of the magnification is determined such that the size of the image of the capillary core at the entrance aperture (D) is related to the size of the capillary itself (d) by $D=d*f2/f1$. This ensures that the image of the end facet of capillary waveguide 12 "fits" into the entrance aperture of spectrometer 36 with optimal optical coupling. The focal lengths of the two lenses 28, 34 can now be determined by the magnification factor and the physical sizes of components in the system. The focal length of lens 28 (f1) must be chosen to be large enough such that the focus of lens 28 reaches the end facet of capillary waveguide 12 inside the pressurized windowed flange 16. The focal length of lens 34

(f2) must be long enough such that the focus of lens 34 reaches the entrance aperture given the finite size of housings and appurtenances on the front of spectrometer 36. The two lenses 28, 34 are positioned a distance apart equal to the sum of their focal lengths (f1+f2). The sum of the two focal lengths must be greater than the width of the housing of beamsplitter 30 and the housing used to hold laser rejection filter 32. In general, f1 is chosen to be as short as possible given these constraints and f2 is then chosen to provide the proper magnification, again subject to these constraints. Such choices will intrinsically result in optimal matching of the largest quantity of collectable Raman power that can be extracted from a given waveguide and directed into a given detector. The diameter of both lenses must be large enough to pass the full diameter of the collimated Raman beam (or the portion of that which may be refocused into the detector without overfilling its aperture).

Once the imaging system (lenses 28, 34) has been specified as optimal, the remainder of the components can be specified. The mirror 20 must be chosen such that it reflects light from the output end-facet of capillary waveguide 12 in flange 22 at a numerical aperture or angle greater than or equal to the numerical aperture being collected at the other end of capillary waveguide 12. This implies a combination of size and focal length for mirror 20. The minimal focal length is chosen such that the focus of mirror 20 can be placed at the end facet of capillary waveguide 12 after having passed through the optical window 24 given the finite length of the flange 22. This also implies the minimum size for mirror 20, which is chosen only to reduce cost.

The optical compressor 10 is next chosen to provide optimal coupling of the pump-laser beam into capillary waveguide 12. In order to propagate with the lowest possible loss, the pump beam must propagate in low order-waveguide modes. These modes are known as the $TE_{0n}$ modes. These modes are azimuthally polarized, and contain radial distributions with null-points at the waveguide walls. In order to efficiently couple into these waveguide modes, an azimuthally polarized pump-laser beam must be provided at the input of capillary waveguide 12 with a beam-launch angle that is smaller than the propagation angles of the first few $TE_{0n}$ modes (where n in this case is a small integer number—less than about 10). Since the focal-length f1 for lens 28 has already been specified, the diameter of the collimated pump beam must be specified such that the launch angle condition is met. This is accomplished by specifying an optical compressor 10 that will reduce the diameter of the collimated pump-beam before it reaches lens 28 and is focused into capillary waveguide 12. One must determine the optimal launch angle from the known properties of the $TE_{0n}$ modes. Although coupling into the first few $TE_{0n}$ modes will provide relatively low-loss transmission, coupling all of the pump power into the $TE_{01}$ mode will provide the lowest loss and highest throughput, as is the goal in the exemplary embodiment. Then, given a particular pump-laser with a particular output beam diameter, and given a lens 28, one can specify the compression ratio by which to reduce the pump-beam diameter and meet the launch angle requirement.

In most commercially available lasers, a beam is produced with linear polarization due to the properties of the laser cavity components. Ideally, a laser with an azimuthally polarized output is desired because it will propagate with the lowest loss through capillary waveguide 12, and will produce Raman signals (in gases with low depolarization ratios) that are also mostly azimuthally polarized and will themselves experience the lowest loss in waveguide capillary 12. In the illustrated embodiment, pump laser 4 is such a laser and produces a linearly polarized laser beam. Thus, according to one aspect of one exemplary embodiment of the invention, and as described elsewhere herein, the linearly polarized laser beam is passed through linear to azimuthal polarization converter 8. Linear to azimuthal polarization converter 8 efficiently converts the linear polarization into an azimuthal or "circular TE" (transverse electric) polarization. The resultant beam, referred to herein as a TE polarized-beam, exhibits electric field lines which appear as circular concentric rings. Linear to azimuthal polarization converter 8 may be, for example and without limitation, a liquid-crystal polarization converter such as is commercially available from Arcoptix S.A. of Neuchâtel, Switzerland, or a specially designed pie-cut ½ waveplate device as described in Machavariani et. al., *Efficient Extracavity Generation of Radially and Azimuthally Polarized Beams*, Optics Letters, Vol. 32, Issue 11, pp. 1468-1470 (2007). In the exemplary embodiment, linear to azimuthal polarization converter 8 provides the lowest possible transmission loss to the pump beam, while also providing a high ratio of the desired polarization to all other polarizations. The azimuthal beam is then launched into hollow metal-lined capillary waveguide 12 which contains the Raman active test-gases using the optical train that is described in detail elsewhere herein. Raman photons therefore couple into azimuthally polarized (TE) waveguide modes, which exhibit less loss than their linearly polarized counterparts—the EH modes. This coupling into azimuthal circular electric modes (TE waveguide modes) allows the Raman light to experience less loss, and allows gas detection system to output higher Raman power (as much as 8 times as much power in one configuration) than would be possible using a linearly-polarized pump laser beam, and will result in significantly improved detection. Of course, in an alternative embodiment, linear to azimuthal polarization converter 8 may be omitted, in which case the Raman signals will be caused to couple into linearly polarized waveguide modes.

Furthermore, a hollow waveguide with a reflective lining, such as capillary waveguide 12, must be constructed using some sort of substrate or wall-material to support the reflective lining. In many cases, this wall material is solid silica glass. When a pump laser beam leaks into the solid wall material due to waveguide losses or non-ideal pump-launch conditions, the glass walls of the waveguide itself emit Raman photons. The Raman signal from the waveguide walls is generally broadband and continuous due to the amorphous nature of the silica glass in the waveguide walls. The strength of this signal is usually large due to the solid density of the silica glass being much greater than the usual density of gases being sampled in the waveguide core. In other cases, waveguide coatings are made from polyimide plastics which can fluoresce when leakage from the pump laser passes through such an exterior plastic coating. Both of these sources of noise must be reduced or eliminated in order to maintain high signal-to-noise ratios in gas detection system 2. Similarly, other sources of noise such as stray light from the environment or other emissions from nearby optical components can be introduced into the leaky-guiding wall-region of a waveguide that is constructed of a transparent wall substrate, like a solid silica glass capillary. Thus, a number of different spatial filtering techniques are described herein to reduce the optical sources of noise which are likely to be present in a waveguide-based sensor system such as gas detection system 2.

More specifically, the scattered light which is collected by capillary waveguide 12 must be spectrally separated and its power measured to determine the concentration of each gas present in capillary waveguide 12. Traditionally, this light would have been measured using a dispersive spectrometer. A dispersive spectrometer uses either a multichannel detector surface (like a CCD camera, diode array, or CMOS array) with a fixed dispersive element (like a grating or prism) or a single-channel detector (like a photodiode) with a moveable scanning grating to measure a portion of the optical spectrum covering the output-wavelengths of several gas species. The use of a slow movable grating in gas detection system 2 is impractical for most applications due to the short measurement times that are required (e.g., less than one second in the case of large natural gas-fired turbine electricity generators as described elsewhere herein). Instead, as described elsewhere herein, gas detection system 2 in the exemplary embodiment employs dispersive imaging fixed-grating spectrometer 36 (a fixed-dispersive element) and 2-dimensional CCD camera 38, which allows the implementation of digital-spatial-filtering algorithms described below to reduce system noise.

In particular, in this exemplary embodiment, gas detection system 2 is configured to produce an image of the end facet of capillary waveguide 12 at the input aperture of spectrometer 36. In the illustrated embodiment, 2D CCD camera 38 is placed at the output aperture of spectrometer 36, and a spectrally-dispersed image of the end-facet of capillary waveguide 12 appears at 2D CCD camera 38. The spectrally-dispersed image of end-facet of capillary waveguide 12 contains both gas-Raman signals and silica-Raman noise from the substrate of capillary waveguide 12. An image segmentation or filtering algorithm, implemented in a computing device 39, such as, without limitation, a PC or server computer or dedicated control and processing electronics, coupled to the 2D CCD camera 38, is applied to the CCD pixel data of the spectrally-dispersed image of end-facet of capillary waveguide 12 to subtract out most of the silica Raman noise while leaving the majority of the gas-Raman signal, thus improving the signal to noise ratio. In the exemplary embodiment, computing device 39 includes a processing unit including a processor, such as a microprocessor or microcontroller, and a suitable memory that stores software executable by the processing unit for performing the processing and algorithms described herein. In the simplest case, several rows of pixels near the center of the spectrally-dispersed image of the end-facet of capillary waveguide 12 are summed together and constitute the output signal, while the remaining (mostly noise) rows of pixels are discarded. In a more robust version of the algorithm, a circular-shaped morphological filter which approximates the shape of the useful portion of the output of capillary waveguide 12 is scanned across the 2D pixel array data of the spectrally-dispersed image of end-facet of capillary waveguide 12 and is used to discriminate between signal and noise data.

Figure 2:
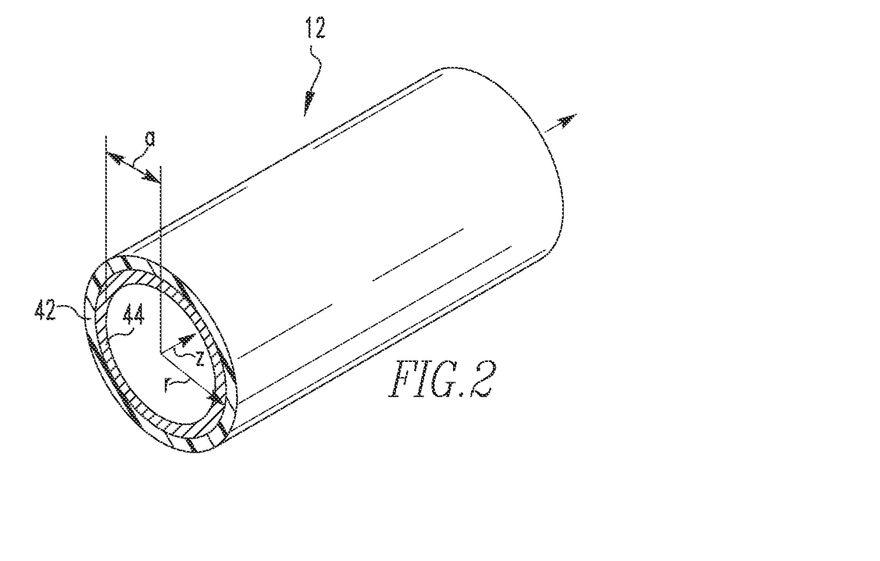
FIG. 2 is an isometric view of a portion of an exemplary capillary waveguide forming a part of the gas detection system of FIG. 1.
Figure 3:
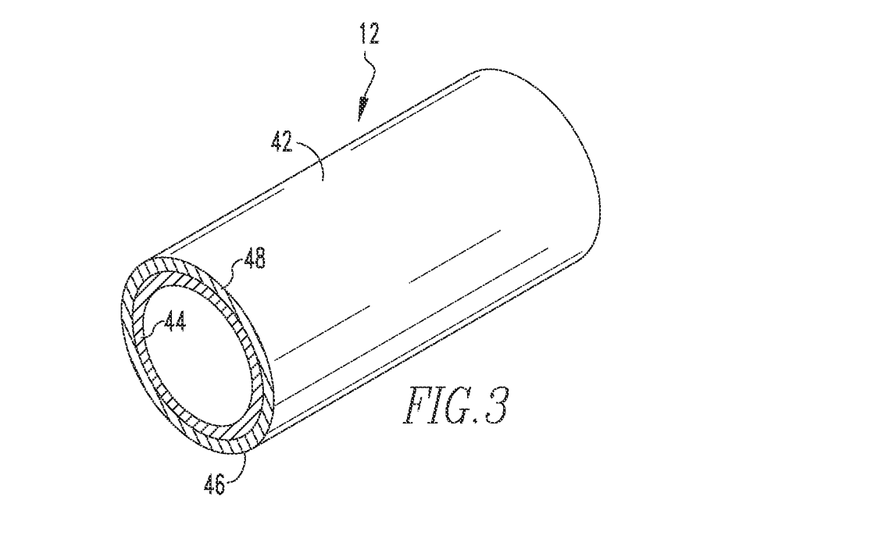
FIG. 3 is an isometric view of a portion of an alternative exemplary capillary waveguide forming a part of the gas detection system of FIG. 1.

In a further aspect of an exemplary embodiment of the invention, a method of removing or blocking a large amount of optical noise which is produced in hollow metal-lined capillary waveguide 12 has been designed. Blocking this noise is important to maintaining a high SNR. FIG. 2 is an isometric view of a portion of an exemplary capillary waveguide 12 that includes glass walls 42 and metal lining 44. A majority of silica Raman and fluorescent noise was determined to emanate from the solid glass-walls 42 of capillary waveguide 12 itself, as well as from the coating surrounding glass walls 42. Referring to FIG. 3, to eliminate the noise, end-facet portion 46 of glass walls 42 of capillary waveguide 12 is coated with a thick (several µm or more in thickness) reflective or absorptive metal layer 48. Metal layer 48 preferably extends from the outside edge of inner metal lining 44 to the outer diameter of the capillary coating or jacket. Metal layer 48 blocks the majority of the silica Raman noise and confines it to the capillary glass-substrate. Various opaque metal coatings are believed to be suitable for metal layer 48 including silver, gold, or aluminum. These metals can be plated on the end-facet (i.e. electrochemical silver plating), sputter-coated on the end-facet, deposited with chemical-vapor-deposition on the end-facet, or simply painted on the end-facet.

Figure 4:
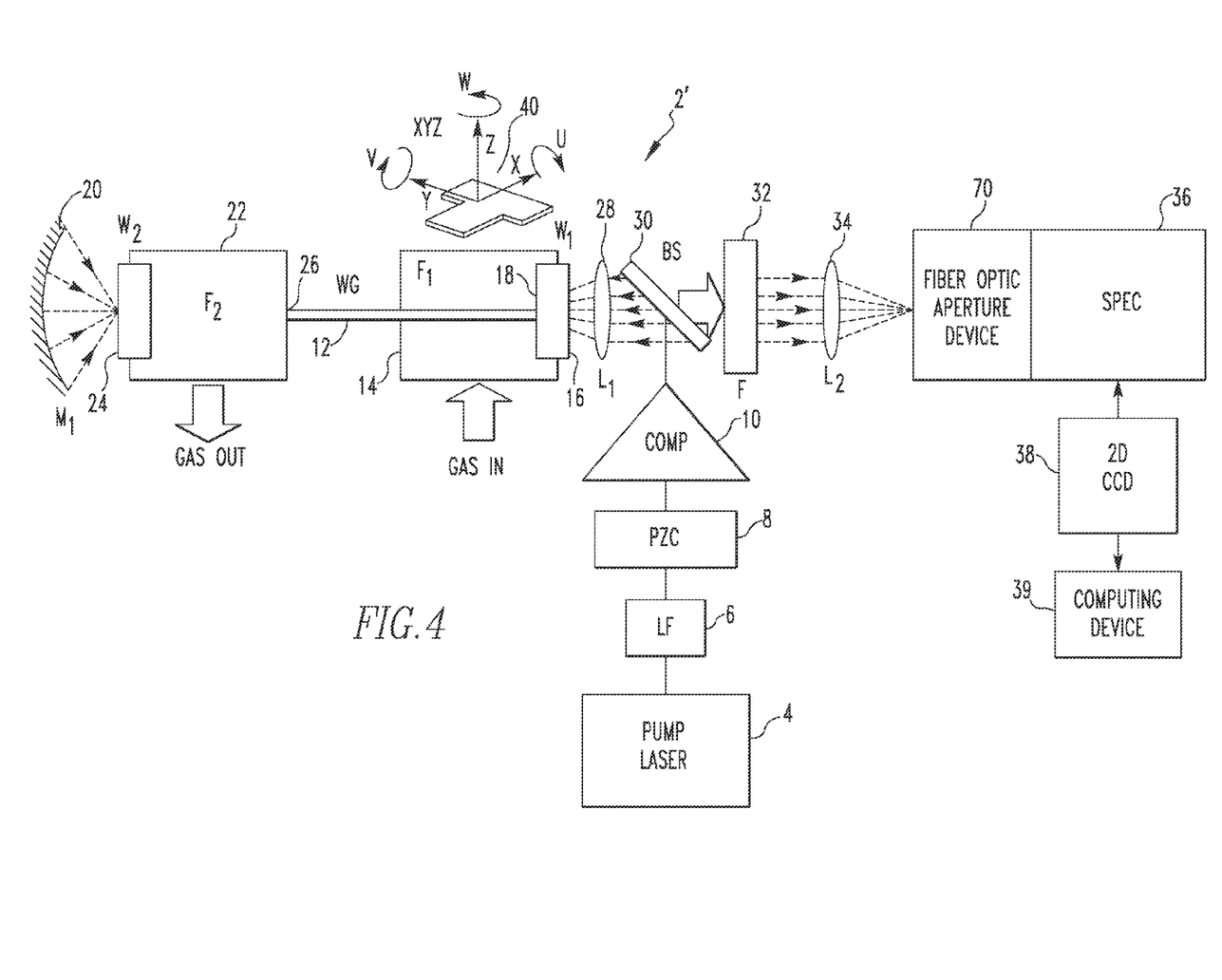
FIG. 4 is a schematic diagram of a gas detection system according to an alternative exemplary embodiment of the present invention.
Figure 5:
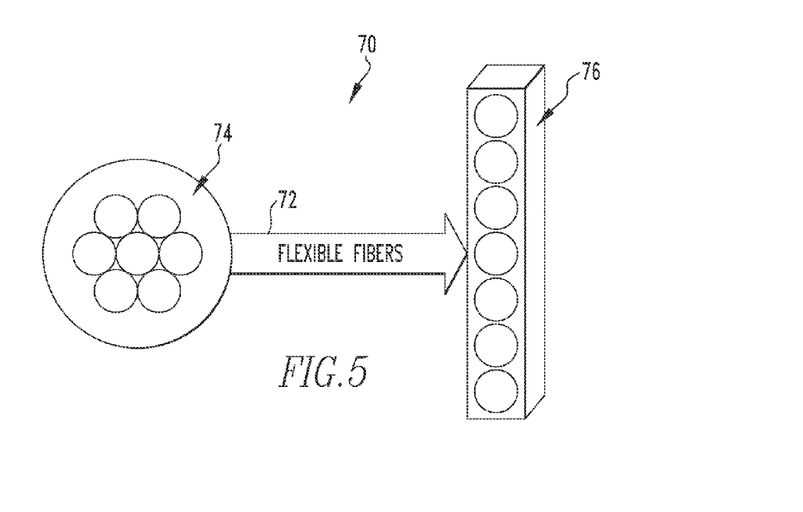
FIG. 5 is a schematic diagram of a fiber optic aperture device forming a part of the gas detection system of FIG. 4.

In another implementation, a physical aperture is inserted into a plane containing an image of the waveguide end-facet which is sized such that the area of the image containing light from the waveguide core is passed through the aperture while light emanating from the portion of the image from the waveguide cladding or walls is blocked. FIG. 4 is a schematic diagram of a gas detection system 2' according to an alternative exemplary embodiment of the present invention that implements such a physical aperture according to one particular embodiment. Gas detection system 2' includes many of the same components as gas detection system 2, and like components are labeled with like reference numerals. As seen in FIG. 4, gas detection system 2' includes a physical aperture in the form of a fiber optic aperture device 70 commonly known as a fiber bundle. FIG. 5 is a schematic diagram of fiber optic aperture device 70. As seen in FIG. 5, fiber optic aperture device 70 includes a plurality of flexible optical fibers 72 that are bundled together. At an input end 74 of fiber optic aperture device 70, flexible optical fibers 72 are arranged in circular configuration, and at an output end 76 of fiber optic aperture device 70, flexible optical fibers 72 are arranged in slit or line configuration. The outer diameter of the circular configuration of the bundle at input end 74 is equal the diameter of the image of the core region of capillary waveguide 12 produced at the focus of lens 34. As used herein, "core region" shall refer to the inner portion of capillary waveguide 12 not including the glass walls or the cladding or any inner metal lining coupled to the glass walls. As seen in FIG. 4, input end 74 of fiber optic aperture device 70 is positioned at the focus of lens 34 in the position that was occupied by spectrometer 36 in gas detection system 2. Output end 76 of fiber optic aperture device 70 is then positioned in the focal plane of the entrance aperture of the spectrometer 36. The effect of fiber optic aperture device 70 is to both allow for increased resolution and collection efficiency while providing an aperture for spatial filtering due to its circular extent. More simply, the noise falls outside the fiber optic aperture device while the signal "fits" into fiber optic aperture device 70, and is transferred to spectrometer 36.

Thus, the present invention provides a gas detection system that is fast, accurate, and capable of continuously measuring and/or reporting the concentrations of gases (or sometimes liquids) in a mixture such as natural gas (which is mostly a mixture of methane, ethane, and propane). In some embodiments, the gas detection system is capable of producing a combination of speed (e.g., a sampling rate of approximately 1 second) and accuracy (<0.1% accuracy with hydrocarbon and other gases) which is not matched by any other known instrument. In addition, in some embodiments, the gas detection system is capable of measuring eight or more gases simultaneously. For example, and without limitation, the gas detection system is capable of detecting methane, ethane, propane, carbon-dioxide, carbon-monoxide, oxygen, nitrogen, butane, ethylene, hydrogen, nitrous-oxide, sulfur-dioxide, ammonia, and any other Raman active gas. The combination of speed, accuracy, and multiple gas measurement makes the gas detection system work particularly well for controlling natural gas fired turbines by measuring the input-fuel composition or filtered exhaust gasses in real-time. Currently, there is no other single sensor which is capable of controlling a gas turbine by measuring the instantaneous combination of all fuel-gases feeding the burner and/or exhaust-gases exiting the turbine.

This present invention is particularly well suited for the monitoring of a mixture of multiple gases for control of a process, reaction, or machine (such as a gas-turbine) with gaseous inputs or outputs. Although an original application of the invention was to measure the gases in a natural-gas pipeline, it is also well suited to controlling various industrial processes or reactions, monitoring out-gassing of any kind, and controlling any form of combustion equipment. In addition, one version of the invention can be used as a new type of detector in gas chromatography systems. The invention may also be useful in the diagnosis of transformer failure via out-gassing studies, the detection of gaseous residues for homeland security purposes, the monitoring of gases exhaled during anesthesia or in the operating room, the monitoring of pollutant gases in smoke stacks, and the detection of flammable gases for mine-safety applications.

Figure 6:
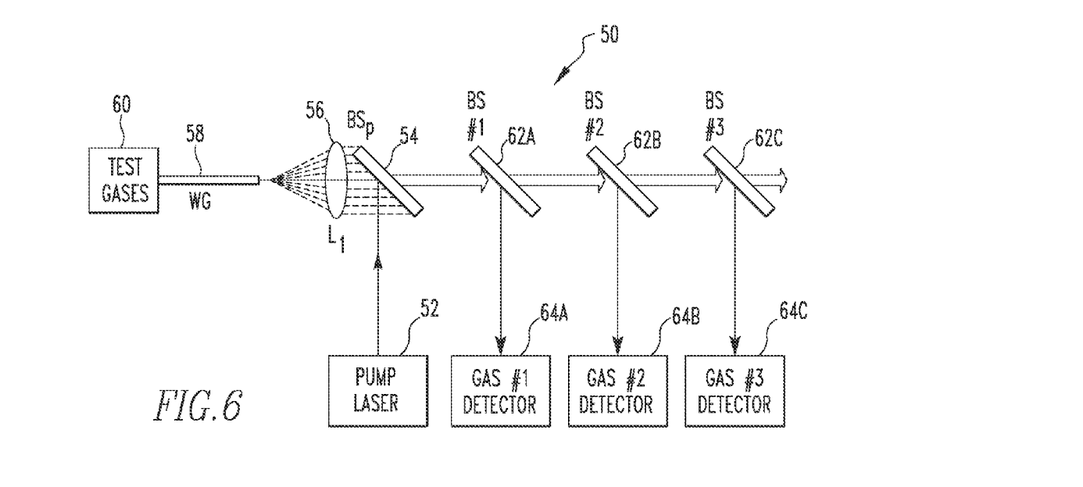
FIG. 6 is a schematic diagram of a gas detection system according to an alternative exemplary embodiment of the present invention.

FIG. 6 is a schematic diagram of a gas detection system 50 according to an alternative exemplary embodiment of the present invention. Gas detection system 50 includes pump laser 52, dichroic long-pass beam splitter 54, lens 56, hollow metal-lined capillary waveguide 58 and gas input flange 60. Gas input flange 60 is used to introduce the gas to be tested into capillary waveguide 58. Beam splitter 54 reflects the pump beam into capillary waveguide 58 through lens 56 and passes the Stokes-shifted gas-Raman signals with low loss generated within capillary waveguide 58 that have been collimated by lens 56.

As seen in FIG. 6, gas detection system 50 also includes a series of dichroic beam splitters 62A, 62B, 62C each positioned at 45 degrees to the optical axis. After the light output from capillary waveguide 58 is collimated by lens 56 and passed through beam splitter 54, the collimated beam passes through this series of dichroic beam splitters. Each dichroic beam splitter 62A, 62B, 62C is a multi-layer dielectric filter designed to reflect a narrow spectral peak corresponding to the Raman peak of a particular gas of interest. A single-channel detector 64A, 64B, 64C (photomultiplier tube, photodiode, etc.) is positioned in the path of the reflected light to measure the signal produced by one particular gas. As shown, many of these single channel/single gas detectors can be incorporated into a single system for simultaneous measurement of a virtually unlimited number of species with high-accuracy. Although a spectrometer is somewhat effective at making these measurements, it cannot measure as quickly as this method. This is because a standard spectrometer equipped with a fixed grating and CCD array detector suffers a tradeoff between resolution and bandwidth. In this configuration, the coatings can be designed for a large range of spectral resolution, and more detectors can be used for increased bandwidth (more species). Finally, the use of dichroic beam splitters instead of a limited-aperture spectrometer allows larger solid-angles (or higher numerical apertures) in the Raman signal path to reach the detectors, which means larger signals can be collected. In one alternative exemplary embodiment, gas detection system 50 may employ the configuration including pump laser 4, cleanup filter 6, linear to azimuthal polarization converter 8, and optical compressor 10, and the configuration including capillary waveguide 12, gas-input flange 14, window 16, spherical mirror 20, gas-output flange 22, window 24, and motion stage 40 as described elsewhere herein (FIGS. 1 and 4) in place of the laser and waveguide shown in FIG. 6.

Figure 7:
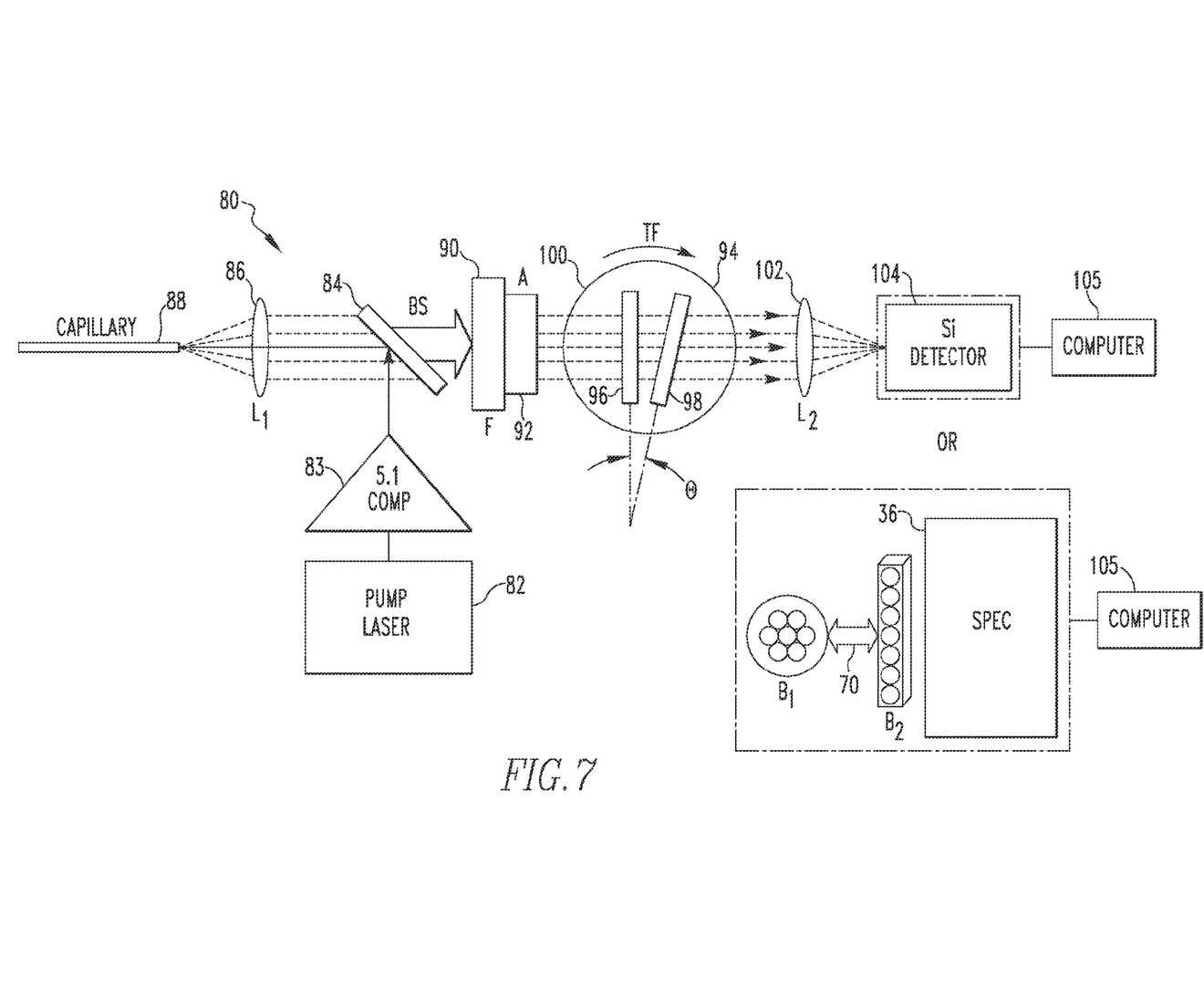
FIG. 7 is a schematic diagram of a gas detection system according to another alternative exemplary embodiment of the present invention.

FIG. 7 is a schematic diagram of a gas detection system 80 according to another alternative exemplary embodiment of the present invention. Gas detection system 80 includes pump laser 82, optical compressor 83, dichroic long-pass beam splitter 84, lens 86, and a hollow metal-lined capillary waveguide 88. The gas to be tested is introduced into capillary waveguide 88. Beam splitter 84 reflects the pump beam into capillary waveguide 88 through lens 86 and passes the Stokes-shifted gas-Raman signals with low loss generated within capillary waveguide 88 that have been collimated by lens 86. A steep long-pass dielectric laser rejection filter 90 and a large diameter aperture 92 are positioned after dichroic beam splitter 84. Gas detection system 80 also includes a tunable, rotatable filter (TF) 94 for wavelength selection. Tunable, rotatable filter 94 includes two filters 96, 98 that are each fixed rigidly to a platform 100 enabling both to rotate simultaneously to scan a range of wavelengths. The two filters 96, 98 are offset by an angle $\theta$ from each other to narrow the effective bandwidth. A lens 102 receives the output of the tunable, rotatable filter 94, and focuses it onto the input of a silicon detector 104. The output of silicon detector 104 is analyzed on a computer 105. In one embodiment, the TF 94 is tilted sinsuoidally in time and the frequency components of the detector's output are used to indicate the presence of a spectral peak. In an alternative embodiment, silicon detector 104 can be swapped for a fiber optic aperture device 70 and spectrometer 36 as described elsewhere herein. In operation, tunable, rotatable filter (TF) 94 is rotated while laser light is launched into capillary waveguide 88, and the constituents of the sample gas can be identified depending upon the wavelengths that are passed and detected by silicon detector 104. In one alternative exemplary embodiment, gas detection system 80 may employ the configuration including pump laser 4, cleanup filter 6, linear to azimuthal polarization converter 8, and optical compressor 10, and the configuration including capillary waveguide 12, gas-input flange 14, window 16, spherical mirror 20, gas-output flange 22, window 24, and motion stage 40 as described elsewhere herein (FIGS. 1 and 4) in place of the laser and waveguide shown in FIG. 7.

While the various exemplary embodiments described herein have been shown as employing metal lined hollow capillary waveguides, one or more of those embodiments may employ other types of hollow waveguides instead of a metal lined hollow capillary waveguide. For example, such other types of hollow waveguides may include hollow-core photonic-bandgap fibers, metal and dielectric lined capillary waveguides, solid metal walled hollow-core waveguides with or without additional metal or dielectric linings, or multi-layer Bragg reflector (or ARROW) hollow waveguides. Waveguides employed in the various exemplary embodiments should provide low optical losses at the pump and Stokes wavelengths of interest, as well as having an inner core diameter large enough to facilitate gas transfer rates to support the desired gas-sampling rate.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas detection system, comprising:
    a light detector;
    a hollow multimode reflective-lined waveguide structured to receive a sample gas, the hollow multimode reflective-lined waveguide including a hollow substrate and a reflective lining supported on an interior of the hollow substrate, the hollow multimode reflective-lined waveguide having one or more low order-waveguide modes, each of the low order waveguide modes having a respective low order propagation angle associated therewith;
    a laser beam generating component structured to generate a collimated laser beam having a predetermined beam diameter; and
    a focusing optical element structured to: (i) receive the laser beam, (ii) focus the laser beam into the hollow multimode reflective-lined waveguide, and (iii) collect Raman signals generated within the hollow multimode reflective-lined waveguide in response to the collimated laser beam interacting with the sample gas and direct the Raman signals toward the light detector, wherein the predetermined beam diameter is such that when the laser beam reaches the focusing optical element, the focusing optical element will cause the focused laser beam to enter the hollow multimode reflective-lined waveguide at an angle that excites at least one of the one or more low order-waveguide modes.

2. The gas detection system according to claim 1, wherein the one or more low order-waveguide modes comprise a plurality of low-loss low order-waveguide modes.

3. The gas detection system according to claim 2, wherein the predetermined beam diameter is such that when the laser beam reaches the focusing optical element, the focusing optical element will cause the focused laser beam to enter the hollow multimode reflective-lined waveguide at an angle that is less than or equal to the low order propagation angle associated with the highest order one of the plurality of low order-waveguide modes.

4. The gas detection system according to claim 1, wherein the laser beam generating component comprises: (i) a pump laser structured to generate an original collimated laser beam having an original beam diameter greater than the predetermined beam diameter, and (ii) an optical compressor operatively coupled to the pump laser, wherein the optical compressor is structured to convert the original collimated laser beam into the collimated laser beam by reducing a size of the original collimated laser beam.

5. The gas detection system according to claim 4, wherein the original. collimated laser beam is linearly polarized and the collimated laser beam is TE polarized, and wherein the laser beam generating component further comprises a polarization-converting element operatively coupled to both the pump laser and the optical compressor and structured to receive the original collimated laser beam and convert the polarization thereof from linear polarization to TE polarization.

6. The gas detection system according to claim 1, wherein the focusing optical element has a focal length f1 and is positioned a distance f1 from an end of the hollow multimode reflective-lined waveguide which is structured to receive the focused laser beam.

7. The gas detection system according to claim 4, further comprising a second focusing optical element structured to focus the Raman signals toward the light detector.

8. The gas detection system according to claim 7, wherein the second focusing optical element has a focal length f2 and is positioned a distance f2 from an aperture of the light detector.

9. The gas detection system according to claim 8, wherein the focusing optical element and the second focusing optical element are positioned a distance apart equal to (f1+f2).

10. The gas detection system according to claim 8, further comprising a dichroic beam splitter structured to reflect the collimated laser beam toward the focusing optical element and pass the Raman signals collected by the focusing optical element toward the second focusing optical element.

11. The gas detection system according to claim 1, wherein the hollow multimode reflective-lined waveguide has a first end and a second end, wherein collimated laser beam is focused into the first end, and wherein the gas detection system further comprises a spherical mirror positioned adjacent the second end of the hollow multimode reflective-lined waveguide, the spherical mirror being structured to redirect laser light and Raman light output from the second end of the hollow multimode reflective-lined waveguide back into the second end of the hollow multimode reflective-lined waveguide.

12. The gas detection system according to claim 1, wherein the light detector comprises a spectrometer.

13. The gas detection system according to claim 1, wherein the hollow multimode reflective-lined waveguide has a first end and a second end, wherein collimated laser beam is focused into the first end, and wherein the gas detection system further comprises a motion stage operatively coupled to the first end of the hollow multimode reflective-lined waveguide and structured to enable selective positioning of the first end of the hollow multimode reflective-lined waveguide with respect to the focusing optical element.

14. The gas detection system according to claim 13, wherein the motion stage is a 2 or more axis motion stage.

15. The gas detection system according to claim 1, wherein an optical coupling efficiency between the hollow multimode reflective-lined waveguide and at least the focusing optical element is invariant to temperature changes.

16. The gas detection system according to claim 1, wherein the focusing optical element comprises a lens.

17. The gas detection system according to claim 1, wherein the reflective lining is a metal lining or a metal and dielectric lining.

18. The gas detection system according to claim 1, further comprising a second focusing optical element structured to focus the Raman signals toward the light detector, wherein the light detector has an étendue, wherein the hollow multimode reflective-lined waveguide has a diameter, wherein the first focusing optical element and the second focusing optical element are optimally chosen to match the étendue and the diameter such that a maximum quantity of Raman power can be extracted from the hollow multimode reflective-lined waveguide and directed into the light detector.

19. A gas detection system, comprising:
    a light detector;
    a hollow multimode waveguide structured to receive a sample gas, the hollow multimode waveguide having one or more low order-waveguide modes, each of the low order-waveguide modes having a respective low order propagation angle associated therewith;
    a laser beam generating component structured to generate a collimated laser beam having a predetermined beam diameter; and
    a focusing optical element structured to: (i) receive the laser beam, (ii) focus the laser beam into the hollow multimode waveguide, and (iii) collect Raman signals generated within the hollow multimode waveguide in response to the collimated laser beam interacting with the sample gas and direct the Raman signals towards the light detector, wherein the predetermined beam diameter is such that when the laser beam reaches the focusing optical element, the focusing optical element will cause the focused laser beam to enter the hollow multimode waveguide at an angle that excites at least one of the one or more low order-waveguide modes, wherein an optical coupling efficiency between the hollow multimode waveguide and at least the focusing optical element is invariant to temperature changes, and wherein the hollow multimode waveguide is fixed at one end in a high-pressure flange and is supported by a support tube, the support tube having an inner diameter that is larger than an outer diameter of the hollow multimode waveguide, thereby allowing the hollow multimode waveguide and the support tube to expand and contract at different rates with changing external temperatures.

20. A gas detection system, comprising:
a light detector;
a hollow multimode waveguide structured to receive a sample gas, the hollow multimode waveguide having one or more low order-waveguide modes, each of the low order-waveguide modes having a respective low order propagation angle associated therewith;
a laser beam generating component structured to generate a collimated laser beam having a predetermined beam diameter; and
a focusing optical element structured to: (i) receive the laser beam, (ii) focus the laser beam into the hollow multimode waveguide, and (iii) collect Raman signals generated within the hollow multimode waveguide in response to the collimated laser beam interacting with the sample gas and direct the Raman signals toward the light detector, wherein the predetermined beam diameter is such that when the laser beam reaches the focusing optical element, the focusing optical element will cause the focused laser beam to enter the hollow multimode waveguide at an angle that excites at least one or more low order-waveguide modes, wherein the hollow multimode waveguide has a first end and a second end, wherein the collimated laser beam is directed into the first end, wherein the first end is maintained at a higher pressure than the second end, wherein the sample gas is introduced into the first end and flows from the first end to the second end where it exits the hollow multimode waveguide.

21. A gas detection method, comprising:
introducing a sample gas into a hollow multimode reflective lined waveguide, the hollow multimode reflective-lined waveguide including a hollow substrate and a reflective lining supported on an interior of the hollow substrate, the hollow multimode reflective-lined waveguide having one or more low order-waveguide modes;
launching a laser beam into the hollow multimode reflective-lined waveguide at an angle such that the laser beam couples into at least one of the one or more low order-waveguide modes;
receiving Raman signals generated within the hollow multimode reflective-lined waveguide in response to the laser beam interacting with the sample gas; and
analyzing the Raman signals and identifying one or more particular gases present in the sample gas.

22. The method according to claim 21, wherein the launching comprises generating a collimated laser beam having a predetermined beam diameter and focusing the laser beam into the hollow multimode reflective-lined using a focusing optical element, wherein the predetermined beam diameter causes the laser beam to be launched at the angle and to be coupled into the at least one of the one or more low order-waveguide modes.

23. The method according to claim 22, wherein the step of generating a collimated laser beam comprises generating an original collimated laser beam having an original beam diameter greater than the predetermined beam diameter and converting the original collimated laser beam into the collimated laser beam by reducing a size of the original collimated laser beam.

24. The method according to claim 22, wherein the step of generating a collimated laser beam comprises generating an original collimated laser beam, wherein the original collimated laser beam is linearly polarized, wherein the collimated laser beam is TE polarized, and wherein the method further comprises receiving the original collimated laser beam and converting the polarization thereof from linear polarization to TE polarization.

25. The method according to claim 22, wherein the focusing optical element comprises a lens.

26. The method according to claim 21, wherein the step of launching comprises launching the laser beam into the hollow multimode reflective-lined waveguide at an angle such that the laser beam couples into the one of the one or more low order-waveguide modes having the lowest order mode.

27. The method according to claim 21, wherein the step of launching comprises launching the laser beam into the hollow multimode reflective-lined waveguide at an angle such that the laser beam couples into a plurality of the one or more low order-waveguide modes.

28. The method according to claim 21, wherein the reflective lining is a metal lining or a metal and dielectric lining.

29. The method according to claim 21, wherein the launching comprises focusing the laser beam into the hollow multimode reflective-lined waveguide using a first focusing optical element, wherein the receiving Raman signals comprises focusing the Raman signals toward a light detector using a second focusing optical element and receiving the Raman signals within the light detector, wherein the light detector has an étendue, wherein the hollow multimode reflective-lined waveguide has a diameter, wherein the first focusing optical element and the second focusing optical element are optimally chosen to match the étendue and the diameter such that a maximum quantity of Raman power can be extracted from the hollow multimode reflective-lined waveguide and directed into the light detector.

* * * * *

UNITED STATES PATENT AND TRADEMARK OFFICE
CERTIFICATE OF CORRECTION

PATENT NO. : 8,674,306 B2
APPLICATION NO. : 13/300988
DATED : March 18, 2014
INVENTOR(S) : Joel Falk et al.

It is certified that error appears in the above-identified patent and that said Letters Patent is hereby corrected as shown below:

Title page, second column, OTHER PUBLICATIONS, line 2, "Scattering—based" should read --Scattering-based--.
Title page 2, first column, References Cited, OTHER PUBLICATIONS, line 27, "10. Komachl," should read --Komachl--.

In the Specification
Column 3, line 58, "plurality dichroic beam splitters" should read --plurality of dichroic beam splitters--.
Column 4, line 5, "direct" should read --and direct--.
Column 4, line 53, "may employed" should read --may be employed--.
Column 4, line 64, "As employed, herein," should read --As employed herein,--.
Column 6, line 66, "waveguide 412" should read --waveguide 12--.
Column 8, line 30, "1/2angle" should read --1/2 angle--.
Column 12, line 30, "equal the" should read --equal to the--.
Column 14, line 24, "sinsuoidally" should read --sinusoidally--.

In the Claims
Column 18, Claim 22, line 10, "reflective-lined using" should read --reflective-lined waveguide using--.

Signed and Sealed this
Seventeenth Day of June, 2014

Michelle K. Lee
*Deputy Director of the United States Patent and Trademark Office*